United States Patent
Statham et al.

(10) Patent No.: US 11,948,470 B2
(45) Date of Patent: Apr. 2, 2024

(54) ARTIFICIAL INTELLIGENCE ASSISTANCE TO CHANGE BIOMECHANICAL LOADING

(71) Applicant: ATO-GEAR HOLDING B.V., Eindhoven (NL)

(72) Inventors: Andrew Edward Statham, Eindhoven (NL); Hendrik Frederik Jan Rutjes, Eindhoven (NL); Jurgen Johannes Adrianus Van Den Berg, Helmond (NL)

(73) Assignee: ATO-GEAR HOLDING B.V., Eindhoven (NL)

( * ) Notice: Subject to any disclaimer, the term of this patent is extended or adjusted under 35 U.S.C. 154(b) by 883 days.

(21) Appl. No.: 16/609,866

(22) PCT Filed: May 2, 2018

(86) PCT No.: PCT/EP2018/061232
§ 371 (c)(1),
(2) Date: Oct. 31, 2019

(87) PCT Pub. No.: WO2018/202731
PCT Pub. Date: Nov. 8, 2018

(65) Prior Publication Data
US 2020/0078638 A1 Mar. 12, 2020

(30) Foreign Application Priority Data
May 2, 2017 (GB) ...................... 1706907

(51) Int. Cl.
*A61B 5/103* (2006.01)
*A61B 5/11* (2006.01)
(Continued)

(52) U.S. Cl.
CPC .......... *G09B 19/0038* (2013.01); *A61B 5/103* (2013.01); *A61B 5/1038* (2013.01);
(Continued)

(58) Field of Classification Search
CPC ....... A61B 5/103; A61B 5/1038; A61B 5/112; G06F 17/18; G06F 19/003
(Continued)

(56) References Cited

U.S. PATENT DOCUMENTS

| 8,348,809 B2 | 1/2013 | van der Zande et al. |
| 2012/0078127 A1* | 3/2012 | McDonald ........... A61B 5/4866 600/301 |

(Continued)

FOREIGN PATENT DOCUMENTS

| JP | 2009-254788 A | 11/2009 |
| JP | 2013-013667 A | 1/2013 |

(Continued)

OTHER PUBLICATIONS

Benno M. Nigg, Biomechanics, Load Analysis and Sports Injuries in the Lower Extremities, Sports Medicine, vol. 2, Issue 5, pp. 367-379, 1985.

(Continued)

*Primary Examiner* — Robert P Bullington
(74) *Attorney, Agent, or Firm* — DENTONS US LLP

(57) ABSTRACT

A system configured to generate a motion adjustment instruction for a user performing an action is provided. The system comprises: a target module configured to obtain a target biomechanical load distribution for the user, a sensor arrangement configured to monitor the motion of the user so as to obtain monitored motion data, a monitoring module configured to calculate a monitored biomechanical load distribution for the user in accordance with the monitored motion data, an adjustment module configured to calculate a target adjustment to the motion of the user that corresponds to a reduction of a deviation of the monitored biomechanical load distribution from the target biomechanical load distribution, and an instruction module configured to generate a (Continued)

motion adjustment instruction in accordance with the target adjustment.

25 Claims, 8 Drawing Sheets

(51) Int. Cl.
*G06F 17/18* (2006.01)
*G09B 19/00* (2006.01)

(52) U.S. Cl.
CPC .............. *A61B 5/112* (2013.01); *G06F 17/18* (2013.01); *G09B 19/003* (2013.01)

(58) Field of Classification Search
USPC ............................................................ 482/1
See application file for complete search history.

(56) References Cited

U.S. PATENT DOCUMENTS

| | | | |
|---|---|---|---|
| 2016/0006758 A1 | 1/2016 | Holt | |
| 2016/0067584 A1* | 3/2016 | Giedwoyn | G16H 40/67 700/91 |
| 2017/0303827 A1 | 10/2017 | Giedwoyn et al. | |

FOREIGN PATENT DOCUMENTS

| | | |
|---|---|---|
| JP | 2016-508787 A | 3/2016 |
| JP | 2016-528943 A | 9/2016 |
| JP | 2017-000522 A | 1/2017 |
| WO | 2014/121011 A2 | 8/2014 |
| WO | 2014/197443 A | 12/2014 |
| WO | 2016/199350 | 12/2016 |

OTHER PUBLICATIONS

Thad E. Wilson and Craig G. Crandall, Effect of Thermal Stress on Cardiac Function, Exerc. Sport Sci. Rev., vol. 39, No. 1, pp. 12-17, 2011.

Rasmus Oestergaard Nielsen et al., "Excessive Progression in Weekly Running Distance and Risk of Running-related Injuries: an Association Modified by Type of Injury", Journal of Orthopaedic & Sports Physical Therapy, vol. 44, No. 10, pp. 739-747.

Daniel E. Lieberman et al., "Foot strike patterns and collision forces in habitually barefoot versus shod runners", Nature Letters, vol. 463, Jan. 2010, doi: 10.1038/nature08723, pp. 531-535.

Loring B. Rowell et al., "Reductions in Cardiac Output, Central Blood Volume, and Stroke Volume with Thermal Stress in Normal Men during Exercise", Journal of Clinical Investigation, vol. 45, No. 11, 1966, pp. 1801-1816.

International Search Report issued in International Application No. PCT/EP2018/061232 dated Jul. 26, 2018.

Written Opinion of the International Searching Authority issued in International Application No. PCT/EP2018/061232 dated Jul. 26, 2018.

Japanese Office Action and Search Report issued in connection with related Japanese Patent Application No. 2020-512080 dated Mar. 7, 2022 with English translations.

\* cited by examiner

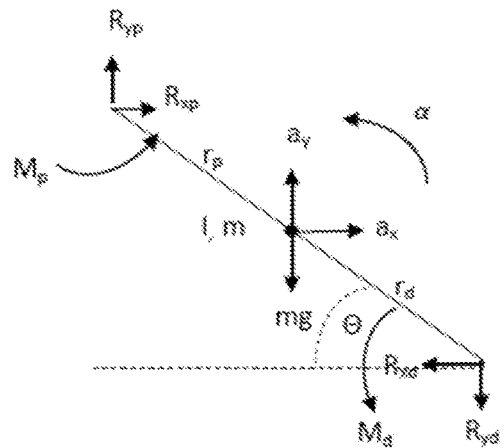

$a_x$, $a_y$ = acceleration of segment COM
$\Theta$ = angle of segment
$\alpha$ = angular acceleration of segment
$R_{xd}$, $R_{yd}$ = reaction forces acting at distal end of segment.
$R_{xp}$, $R_{yp}$ = forces acting on proximal end of segment
$M_d$ = net muscle moment acting at distal joint
$M_p$ = net muscle moment acting at proximal joint
$I$ = moment of inertia about the segment COM
$m$ = mass of segment
$g$ = acceleration due to gravity The resulting forces and torques/moments about the COM are related by the equations of motion 1. $\Sigma F_x = m.a_x$
$R_{xp} - R_{xd} = m.a_x$ 2. $\Sigma F_y = m.a_y$
$R_{yp} - R_{yd} - m.g = m.a_y$ 3. $\Sigma M = I.\alpha$
$M_d - R_{yd}.r_d.\cos\Theta - R_{xd}.r_d.\sin\Theta + M_p - R_{yp}.r_p.\cos\Theta - R_{xp}.r_p.\sin\Theta = I.\alpha$

*FIG. 4*

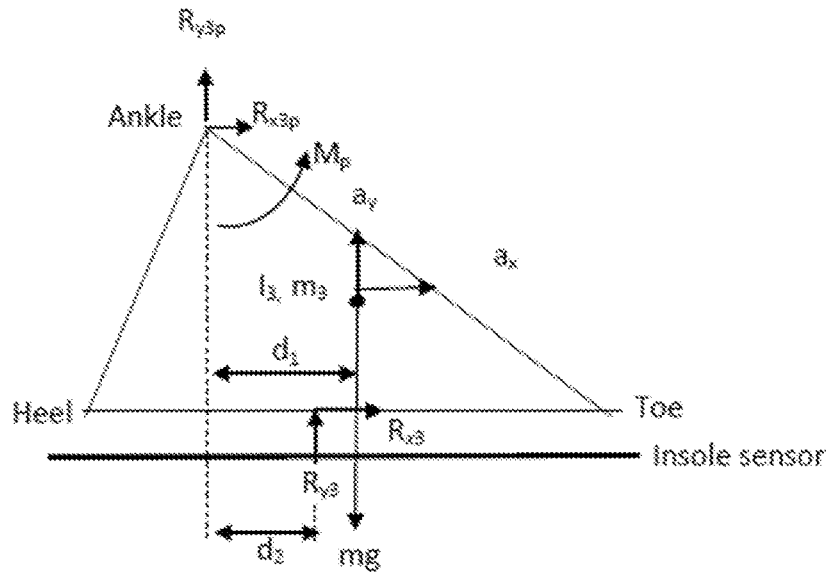

$a_x$, $a_y$ = acceleration of segment COM
$R_{x3}$, $R_{y3}$ = reaction forces acting at centre of pressure (COP)
$R_{x3p}$, $R_{y3p}$ = forces acting on proximal end of segment
$M_p$ = net muscle moment acting at proximal joint
$d_1$ = distance of COP from ankle joint
$d_2$ = distance of COM from ankle joint
$I_3$ = moment of inertia about the segment COM
Insole sensor = spatially distributed pressure sensors embedded in an insole

FIG. 5

Physiological parameters
Heartrate

Biomechanical parameters (user controllable)
Cadence
Stride length
Strike index
Knee flexion
Balance (left/right)
Heel lift height
Speed Biomechanical parameters (not user controllable)
Pronation
Contact time
Impulse
Biomechanical load distribution (estimated forces and torques/moments):
- Left Foot segment distal end force (ankle load)
- Left Foot segment distal end moment (plantarflexor/dorsiflexor load)
- Right Foot segment distal end force (ankle load)
- Right Foot segment distal end moment (plantarflexor/dorsiflexor load)
- Left Lower leg segment distal end force (knee load)
- Left Lower leg segment distal end moment (knee flexor/extensor load)
- Right Lower leg segment distal end force (knee load)
- Right Lower leg segment distal end moment (knee flexor/extensor load)
- Left Upper leg segment distal end force (hip load)
- Left Upper leg segment distal end moment (hip flexor/extensor load)
- Right Upper leg segment distal end force (hip load)
- Right Upper leg segment distal end moment (hip flexor/extensor load)
- Left Lower Back segment distal end force (lumbar load)
- Left Lower Back segment distal end moment (lumbar flexor/extensor load)
- Right Lower Back segment distal end force (lumbar load)
- Right Lower Back segment distal end moment (lumbar flexor/extensor load)

FIG. 7

ARTIFICIAL INTELLIGENCE ASSISTANCE TO CHANGE BIOMECHANICAL LOADING

CROSS-REFERENCE TO RELATED APPLICATIONS

This application is a National Stage of PCT/EP2018/061232, filed May 2, 2018, which claims priority under 35 U.S.C. § 119 to GB Application No. 1706907.1, filed May 2, 2017, all of which are incorporated herein by reference in their entirety.

FIELD OF THE INVENTION

The present invention relates to a system and method to generate a motion adjustment instruction for a user. The invention is applicable to an action such as a sporting activity or form of exercise, for example running, wherein a person would typically employ a coach to help them alter their technique for that sporting activity or form of exercise.

BACKGROUND TO THE INVENTION

Many forms of exercise involve sporting activity and one example is running. There are systems that assess the overall mechanical load during training and give advice on the type of training to be attempted in the next training session in order to optimise the training effect (e.g. U.S. Pat. No. 8,348,809). However, such systems make recommendations based on accumulated work done and do not help the user alter their style of running. There are many different reasons why some people choose to run. Runners do not want injury to curtail their running activity and runners who compete will want to improve their performance. There are many different styles of running and runners generally adopt a style without realising how it can affect performance or injury risk. Running style is determined by many factors that a person can control such as body position, placement of feet and joints during running and type of equipment such as shoe, insole or knee brace for example. Typical examples where the user has direct control are cadence, stride length, what part of the foot makes initial contact, flexing of knees for softer landing, pre-tension of muscles prior to landing, leaning forward or backward, vertical oscillation (bounciness), balance (spending more time and/or pushing harder on left or right foot), pelvic rotation and core muscle activity such as tensing abdominal muscles. A runner is often not aware of all these aspects of their style and usually does not know what aspect to change in order to gain the benefit they desire. Thus, if they want to improve performance or reduce risk of injury while running, they would typically get help from a human coach or personal trainer. The coach will usually observe the person running and may perform tests to assess capabilities and then provide advice on what the person should do to improve their running technique in the next running session. This advice is often based on experience and intuition but if the person is running on a purpose-designed treadmill fitted with multiple sensors and the coach is alongside the runner, the coach may be able to feedback suggestions to the runner based on physical metrics such as cadence, heart rate, oxygen consumption and impact forces on the platform for example. However, if the person is running on a track, road or trail, it is difficult for the coach to assess if the runner is succeeding in making small changes in style other than by looking at the overall performance and interviewing the person after the run. When the person is running in natural running environments "in the field", the coach cannot measure instantaneous parameters or feedback corrective suggestions during the run. Therefore it would be desirable to have a portable apparatus that could provide instructions, then measure and monitor progress, ideally during the activity, to teach a person how to change their style or technique in order to achieve a specific change in the distribution of forces in the body while executing an activity.

SUMMARY OF THE INVENTION

In accordance with a first aspect of the invention there is provided a system configured to generate a motion adjustment instruction for a user performing an action, the system comprising: a target module configured to obtain a target biomechanical load distribution for the user, a sensor arrangement configured to monitor the motion of the user so as to obtain monitored motion data, a monitoring module configured to calculate a monitored biomechanical load distribution for the user in accordance with the monitored motion data, an adjustment module configured to calculate a target adjustment to the motion of the user that corresponds to a reduction of a deviation of the monitored biomechanical load distribution from the target biomechanical load distribution, an instruction module configured to generate a motion adjustment instruction in accordance with the target adjustment.

Advantageously, the system has the capability to use monitored motion data that contains an indication or measure of the motion of a part or parts of the body of a user performing an action to infer or estimate the forces to which the body of the user is subjected while they are performing that action, and how those forces are distributed throughout the body, and in particular the musculoskeletal system, of the user. The system can then use this inference or estimate of the distribution forces throughout the body, that is the biomechanical load distribution for the user, in view of a target biomechanical load distribution which may represent a particular or predetermined distribution of force throughout the body that the user wishes to achieve or which has been calculated or determined to be beneficial in some way, to identify a change the user can make to the manner in which they perform the action which will result in their experienced load distribution being corrected towards the target biomechanical load distribution. The system may then provide the identified change in the manner of execution to the user in the form of a motion adjustment instruction.

The system therefore enables a user to receive instructions that are based upon monitored properties of their execution of the action or a particular exercise, and provide an indication to the user of how they may change that manner of execution in order that the biomechanical load distribution arising from the performing of the action become equal to, or closer to, their target biomechanical load distribution.

The motion adjustment instruction may be derived from the target adjustment, so that the instruction informs the user how they may achieve the target adjustment, for example by way of making conscious changes to the way they perform the action.

The motion adjustment instruction may be generated in accordance with the target adjustment in the sense that the motion adjustment instruction includes an indication of the target adjustment. The indication may thus be detailed so as to instruct the user as to what change should be made to their action execution in order to achieve or progress or correct the biomechanical load distribution resulting from them performing the action towards the target biomechanical load distribution. In other embodiments, the indication may be more rudimentary in nature, and may comprise a simple indicator that one or more parameters of the motion of the user are within or outside of a range of values corresponding to a change in motion that will bring the user closer to the target biomechanical load distribution.

The indication may be in any of a variety of forms, for example a verbal, textual or audio message indicating for instance a parameter of the execution of the action that the user is able to adjust. The indication may in some embodiments comprise a visual indication that may be provided to a user by way of illuminating one or more LEDs or by way of an icon or message presented on a digital display.

The motion adjustment instruction may therefore indicate to the user how they should adapt their manner of performing the action, either in a manner that explicitly indicates the target adjustment, or in a way that implicitly indicates it. For instance, when a target adjustment includes the user decreasing the velocity with which their feet impact the ground, the system may provide an implicit indicator that a user should decrease their running speed in the form of the illumination of a coloured LED which the user interprets as a signal to slow down. In other examples, the same target adjustment may be more explicitly indicated by a textual message delivered to a user instructing them to slow their speed, or more explicitly still explaining that their foot impact level is too great and should be reduced.

The system may be implemented as a wearable system and apparatus that provides interactive instruction to help a user change the technique they use for a sporting activity in order to make a specific change to the distribution of any of the forces, moments, and torques within the body during that activity.

The system, which may be thought of as a coaching system, is typically implemented with apparatus that can measure or derive a number of physiological and/or biomechanical parameters while the user is conducting the sporting activity or form of exercise and may allow input from the user and provide feedback to the user.

The algorithms that are typically used may be implemented in an artificial intelligence advice module that is some form of embedded computing device. In some embodiments the action, sporting activity, or form of exercise is related to running. However, it will be appreciated that the action for which the system is used may be any of a number of other types of activity. The system may be capable of obtaining monitored motion data from a sensor arrangement and generating a motion adjustment instruction in connection with any user action for which a biomechanical load distribution arising from the activity can be calculated based upon the measured or monitored motion corresponding to that activity.

In some embodiments, the system further comprises a user interface configured to provide the motion adjustment instruction to the user. The user interface may comprise a device for providing any of visual, audible, haptic, or other forms of information or signal to a user that may indicate a motion adjustment instruction. Such user interfaces may be wearable or attachable to the person, that is the body or clothing, of a user so that they may be worn or attached to the user during the performing of the action. This allows motion adjustment instructions to be provided in the manner of feedback upon performance, so as to allow the user to adjust their execution of the action, while they are performing the action, in response to the instructions.

In some embodiments, the system may be configured to provide the motion adjustment instruction to the user by way of an external user interface or information delivery device.

For example, the system may comprise a data connection such as a wireless transmitter or transceiver, for example a Bluetooth interface, configured to transmit data to a receiving device. The transmitted data may comprise the motion adjustment instruction. The system may be configured to transmit such data to a computing device such as a smart phone which itself may be configured to receive the instruction and present it to a user.

While these embodiments are advantageous for providing near-instantaneous, or "live" motion adjustment instruction feedback to a user while they are performing the activity, some embodiments may be configured to store data which may comprise motion adjustment instructions, and may also comprise the other data processed by the system, in a storage device which may be part of the system or external to it, in order for the data or instructions to be reviewed later or after the action has been performed.

In preferred embodiments, however, the user interface is configured to provide motion adjustment instructions to the user in real time. It will be understood that the term real time relates to the processing or presenting of data in a timescale of the order of milliseconds, for example 50 milliseconds or less, so that the data is available virtually immediately, and so advantageously may be available as feedback to the process from which it is coming.

In some embodiments, the monitoring module is configured to calculate the monitored biomechanical load distribution by calculating values for the magnitude and direction of forces exerted upon a plurality of parts of the body of the user, based upon the monitored motion data and using a computational mechanical model of the body.

In this way, the system may use measured values for a particular aspect or particular properties of the motion of the user in performing the action, for example the force or pressure exerted upon, or the linear or rotational velocity or acceleration of a body part to which a sensor is attached, to calculate forces or loads exerted upon parts of the body that may be different from those which are directly monitored by the sensors, by way of representing the body of the user as a mathematical model and calculating the relationships between the biomechanical force distribution and the monitored motion data in accordance with that model.

In some embodiments, the sensor arrangement comprises at least one pressure sensor and is configured to monitor the pressure exerted upon one or more regions of a foot of the user as a result of a contact force exerted upon that foot by the ground during locomotion, and wherein the monitored motion data comprises data representative of the monitored pressure.

For performed actions that involve locomotion, including walking, jogging, or running, by the user, it may be advantageous for the purpose of calculating the monitored biomechanical load distribution to measure or monitor the contact force exerted upon the foot by the ground throughout, or at one or more times or moments during, the foot of the user being in contact with the ground. Contact with the ground in this context typically reverts to indirect, rather than direct contact, since the user will typically be wearing some form of footwear such as shoes or trainers, and so during locomotion, will typically make indirect contact with the ground, or the surface upon which the user is performing the action, through the shoe or trainer, and in particular the sole of the footwear.

In some preferred embodiments, the at least one pressure sensor is positioned or attached, or is configured to be positioned or attached, in the sole of a piece of user footwear. For example, the sensor arrangement may include an inner sole comprising one or more pressure sensors located at one or more positions corresponding to one or more respective locations on the foot of the user. In such embodiments, the sensor arrangement may measure the pressure or the force exerted between the inner sole of the footwear and the foot of the user, at however many locations within the footwear at which a sensor is positioned. This force or pressure data may be used, for example, to calculate the force exerted upon various parts of the body, transmitted through the foot of the user and arising from an impact or period of contact between the foot of the user and the ground.

In some embodiments, the sensor arrangement further comprises an inertial measurement unit configured to monitor the linear acceleration and the rotational rate of the foot of the user, and wherein the monitored motion data comprises data representative of the monitored linear acceleration and rotational rate.

In preferred embodiments, the sensor arrangement is configured, using inertial measurement units, to measure or monitor the linear and/or angular velocity and/or acceleration of a part of the body of the user, such as the foot of a user, and may be configured to do so in one, two, or three spatial axes for each of linear and angular measurements. In some embodiments, an inertial measurement unit (IMU) is included in the sensor arrangement and is attachable to the foot or footwear of a user. For example, an IMU may be configured to be in electronic communication with the other parts of the system and may be provided as an integral part of an inner sole or sole insert for user footwear, or may comprise a clip for a fixing to user footwear, or may be adapted for or have a shape suitable for being secured or positioned within a recess within user footwear.

Thus, in some preferred embodiments, an IMU may be provided for one or both feet of a user performing an action so as to enable the velocity of the feet of the user to be measured, for example during the strike phase and/or the stance phase of a gait cycle, which can be used to calculate the impulse or force exerted upon the feet of the user during the gait cycle, and thereby calculate the forces that are transmitted to other parts of the body of the user and calculate the biomechanical load distribution arising during those parts of the cycle.

In some embodiments, the sensor arrangement comprises a sensor configured to monitor the velocity and orientation of one or more monitored parts of the body of the user during the performing of the action.

In this way, some embodiments may include sensors to monitor the motion of any part of the person of the user to which a sensor may be attached. For example, in addition to, or as an alternative to, the sensors attached to the feet of a user, motion sensors may also be provided in the sensor arrangement which are attachable to or configured to monitor the motion of the arms, hands, head, or torso of a user, for example. The system may be configured to identify the part of the body which it is attached, in use based upon a detected pattern of motion which may be associated with a predetermined body part. Measurements from other parts of the body may be used in collating, using data from a plurality of motion sensors distributed around the body for instance, a collection of data representing the overall movement of the body and/or various parts thereof. This may then be used in conjunction with a computational model of the body of the user in order to calculate the monitored biomechanical load distribution.

Thus, the sensor arrangement may comprise different combinations of sensor types in different embodiments.

Some embodiments may include a pressure sensor configured to monitor pressure exerted upon the foot of the user, and these embodiments may comprise an optional IMU that is attachable to the foot. Some embodiments may comprise a foot pressure sensor with a plurality of IMUs that may be positioned at different parts of the body of the user. Some embodiments may comprise a plurality of IMUs, with no foot pressure sensor. Sensor arrangements comprising each of these sensor type combinations may be capable of calculating the monitored biomechanical load distribution.

Typically, the adjustment module is configured to calculate the target adjustment such that it represents an adjustment of the monitored biomechanical load distribution towards the target biomechanical load distribution.

Advantageously, the system may therefore base the motion adjustment instruction upon an adjustment that has been calculated so as to correct one or more values representing the forces comprised by the monitored biomechanical load distribution towards those values comprised by the target biomechanical load distribution.

Typically, the instruction module is configured to identify one or more parameters defining the motion of the user, and is further configured to generate the motion adjustment instruction by computing, based upon the target adjustment, a change to the value of at least one of the one or more parameters such that the change can be executed by the user in performing the action so as to result in the target adjustment.

In other words, the instruction may be capable of identifying a parameter of the action being performed that the user can consciously control, and which may be adjusted such that the values of the biomechanical load distribution resulting from the action are brought closer to the values of the target biomechanical load distribution. Parameters such as the stride length during running, that is the length of a step, and foot orientation about the transverse axis, that is the pitch of the foot with respect to a direction of locomotion, during the strike phase of the gait cycle, are examples of parameters that may be controlled by a user. Therefore, by relating to the calculated target adjustment to adjustments in such parameters, the instruction module is capable of generating a motion adjustment instruction that includes one or more directions to make such parameter adjustments, using which the user can alter or improve their biomechanical load distribution towards the target by accordingly making those parameter adjustments as they perform the action.

In some embodiments wherein the sensor arrangement comprises a plurality of inertial measurement units, wherein each of the inertial measurement units is attachable to a part of the body or clothing of the user. Each IMU may be configured to monitor the linear acceleration and the rotational rate of the part to which it is attached, and the monitored motion data may comprise data representative of the monitored linear acceleration and rotational rate from each of the plurality of inertial measurement units.

The target biomechanical load distribution may be obtained in a number of ways. In some embodiments, the target biomechanical load distribution may be related to a physiological objective that the user desires to achieve. Thus, the system may further comprise a user input device configured to receive a user input corresponding physiological objective data, and the target module may be configured to obtain the target biomechanical load distribution by calculating the biomechanical load distribution in accordance with physiological objective data received from the input device.

Therefore, the target biomechanical load distribution may be, to some degree, user-configurable, in that user may input a physiological objective, such as a particular part of the body for which they wish to either minimise or maximise the exertion of forces arising from performing the action. The system may calculate the target biomechanical load distribution so as to meet that objective, in that example by maximising or minimising the distribution of load upon the specified body part.

In some embodiments, the system is a programmed processor-based system configured to help a user alter their style of execution of the action, the system further comprising: a storage device for recording sensor values in a log file, an artificial intelligence advice module that is arranged to determine instructions to change parameters that the user can directly influence, and at least one output device for outputting said instructions to said user, wherein the artificial intelligence advice module calculates the current physical state in terms of a profile of measures that includes a biomechanical load distribution for the body and uses it to calculate an instruction that is output to the user; wherein the instruction requires the user to attempt to change at least one parameter in the next time interval and subsequent instructions after the next time interval depend on how the physical state has changed, in order to help the user achieve a particular physical state described by a target profile of measures.

The system may either be set up to be dedicated to one objective or may offer the user a choice of primary objective such as improving performance, injury risk reduction or improving health and fitness. For the chosen objective, the system may offer a selection of more detailed objectives. For running performance, examples are higher speed or longer distance capability. For injury risk reduction, a specific region of the body can optionally be selected, such as foot and ankle or hip and back and type of injury to be avoided such as soft or hard tissue, otherwise an overall minimum risk can be the objective.

For health and fitness, example objectives can be losing weight, muscle tone, hormone stimulation, joint mobility, cardiovascular health or endurance capability for other activities other than running. Thus, the user can in some embodiments define the primary objective for the automated coaching system.

The user may have the option of entering anthropometric data such as height, weight, age, gender or the history of specific injuries, any of which can be used to improve the efficacy of the coaching system.

The system typically includes sensors, electronics and software algorithms that enable it to measure a set of parameters while the user is running, or performing another action.

In use, the user is typically instructed to do a baseline run using their normal running style. During the run, the system collects baseline data for a plurality of physiological and/or biomechanical parameters that are derived from readings from the sensors. The user will typically recognise that they can control some of these parameters directly.

At the end of the baseline run, the system typically constructs a baseline "profile" that is the set of values for individual physiological and/or biomechanical parameters derived from the measurements during the baseline run. A key component of the profile is the "biomechanical load distribution" that shows the distribution of mechanical torques and forces experienced by the anatomical structures or sections of the body that are involved in the activity. The user will not usually know how they can influence the biomechanical load distribution or be aware of this distribution while they are running.

Using this baseline profile and according to the primary objective, the system may then calculate a target profile that the user needs to get close to in order to meet the primary objective. The target profile thus may take account of the capability of the user and what they want to achieve. For example, if the user has indicated they are prone to injury, the target profile will include a biomechanical load distribution where the load is minimised in joints or muscles that are susceptible to injury. If the objective is to maximise performance, the load will be maximised in joints or muscles that are expected to improve performance in the activity or to exercise or stress a specific anatomical structure to stimulate adaptations such as muscle growth. If the objective is to reduce weight, the load will be maximised in specific muscle groups likely to improve calorific burn. If the objective is to improve endurance, the biomechanical load will be distributed more evenly to reduce onset of fatigue in any one muscle group or joint.

The system typically then uses a strategy to calculate a series of instructions to help the user get close to the target profile by altering their style of running or performing the action in question. The system typically instructs the user to focus on changing parameters that the user can control directly. The system can calculate a programme of ordered parameter changes that are likely to move the current user profile closer to the target profile. The system may inform the user of the parameter the user should attempt to change and a goal which is a desired value for this parameter. The goal could involve changing more than one parameter, but only if this is something the user can understand and influence directly.

During the run the system typically records data for a period and uses this data to derive a current profile using the same parameters and biomechanical load distribution metrics as for the baseline profile. The period can be an interval within a run or can be for the total duration of the run. At the end of the period, the system gives feedback to the user and if the period is an interval within a run, the user can make adjustments immediately during the current run. If the user has reached the goal value within a certain range for a sufficient period of the of run, the system typically follows the programme and informs the user of the next parameter they should attempt to change and a goal value for this parameter for the next running period.

This cycle of informing the user of a goal for a running period, reviewing progress and feeding back a new goal for the next running period may be configured to continue until the current profile is sufficiently close to the target profile. The closeness of the profiles can be calculated by a metric such as the sum of weighted squared differences where the weighting can take into account the precision of the parameter measurement and the importance of the parameter to the primary objective.

If the user fails to meet a goal for a running period after multiple attempts, the current coaching strategy may be determined to have failed. In this case, the system typically uses the baseline profile and current profile and uses a different coaching strategy to calculate a new programme of ordered parameter changes. The system may inform the user of the parameter that they should attempt to change and a goal value for the next running period and then follows the new programme for incremental changes.

While attempting to meet a goal, the profile may become "unsafe" for the user in that the analysis of sensor measurements suggests the user is at a higher risk of injury. Furthermore, if performance is to be maintained or increased some changes can make the runner "inefficient" so performance is significantly reduced. Therefore, after each period, the system may be configured to check whether the current profile is "unsafe" or "inefficient" and if so, the current strategy may be terminated. The system typically then suggests that the user do a new baseline run using their normal running style so that a new coaching strategy can be derived taking account of any physiological changes that may have occurred.

There are possible variants to this approach. For example, in some embodiments at the end of each period, the system can use the baseline profile and current profile and recalculate an ordering for the parameter changes so that each parameter change is expected to produce the optimum effect in moving the user closer to the target profile. The system typically then informs the user of the next parameter they should attempt to change and a goal value for this parameter for the next running period. In this approach, the programme is continually refined rather than being changed only when the user is failing to meet one of the goals for incremental change.

An important aspect of some embodiments of the system is that, although it is typically able to measure many parameters that describe a profile for the user, the user may be given specific incremental goals involving just those parameters that they can directly influence by changing their style of running. Although the system is unsupervised in that a human coach is not required, the coaching advice can still reflect best practice gleaned from prior research.

Furthermore, another important aspect is that the system may make continual assessment of risk of injury or reduced performance during the coaching period by using direct and derived measurements from sensors and relating this to results of prior research. This continual assessment of injury risk or reduced performance, the re-calculation of biomechanical load distribution and the option to provide live feedback during the activity is thus beyond what would be achievable by a human coach.

In some preferred embodiments, the system further comprises an artificial intelligence advice module configured to perform a calculation after each time interval to determine the goals for the next parameters that the user should attempt to change to produce the optimum benefit in progress towards the target profile.

The instruction module may typically be configured to estimate the influence on performance during the performing of the action and use it to adjust the motion adjustment instruction.

In some embodiments, the system may comprise an artificial intelligence advice module configured to use a machine learning to calculate the target adjustment and/or to generate the motion adjustment instruction.

In accordance with a second aspect of the invention there is provided a computer implemented method of generating a motion adjustment instruction for a user performing an action, the method comprising: obtaining a target biomechanical load distribution for the user, monitoring, using a sensor arrangement, the motion of the user so as to obtain monitored motion data, calculating a monitored biomechanical load distribution for the user, in accordance with the monitored motion data, calculating a target adjustment to the motion of the user that corresponds to a reduction of a deviation of the monitored biomechanical load distribution from the target biomechanical load distribution, generating a motion adjustment instruction in accordance with the target adjustment.

In some embodiments, the method further comprises providing the motion adjustment instruction to the user.

A biomechanical load distribution may comprise data representative of the distribution within a portion of the body of the user of forces exerted upon the body as a result of the motion of the user. This distribution may therefore be a set of values representative of magnitudes and directions of forces exerted at different parts of, or anatomical structures within, the body of the user, and may also comprise data representing relationships between these forces.

Typically, calculating the monitored biomechanical load distribution comprises calculating values for the magnitude and direction of forces exerted upon a plurality of parts of the body of the user, based upon the monitored motion data and using a computational mechanical model of the body.

It is envisaged that the method will be used to generate motion adjustment instructions pertaining to a variety of different user-performed actions. In particular, the action is typically locomotion and the indication of the target adjustment comprises an instruction to alter the gait of the locomotion. Therefore the generated instruction may comprise an indication of how the user may alter their gait in order that the biomechanical load distribution to be caused to move closer to the target biomechanical load distribution.

Thus, the target adjustment is typically calculated such that it represents an adjustment of the monitored biomechanical load distribution towards the target biomechanical load distribution. Generating the motion adjustment instruction may comprise identifying one or more parameters defining the motion of the user, and computing, based upon the target adjustment a change to the value at least one of the one or more parameters such that the change can be executed by the user in performing the action so as to result in the target adjustment. In other words, the method preferably comprises providing an instruction that, when executed by a user, or caused the biomechanical load distribution throughout their body or throughout a part of it, arising from the performing of the action, to be closer to or equal to the target biomechanical load distribution.

Typically, the monitored motion data comprises an indication of the velocity and/or orientation of one or more monitored parts of the body of the user during the performing of the action. By measuring or monitoring the speed or velocity of one or more user body parts, for example, and using the data collected in a computational mechanical model of the user body, for instance, the biomechanical load distribution may be monitored by relating such recorded motion data to resultant forces distributed in the body using the model.

It may be advantageous, particularly for actions related to running or walking, or any form of locomotion, to monitor the motion of the feet of the user in particular. Therefore, in preferred embodiments, the one or more monitored parts of the body include one or both of the feet of a user, and the monitored motion data for each of the monitored feet comprises an indication of the velocity or orientation of the foot during the stance phase of the gait cycle. Although data may likewise be collected during other phases of the gait cycle, it may be most advantageous to monitor the motion of the feet of the user during the stance phase, when a given foot is in (typically indirect) contact with the ground.

In addition to, or alternatively to, motion data, data indicating the force or pressure exerted between a foot of the user of the running or walking surface or ground, may be used in calculating the monitored biomechanical load distribution. The monitored motion data may therefore further comprise an indication of the pressure exerted on one or more regions of the monitored foot as a result of the contact force exerted upon that foot by the ground during locomotion.

In some embodiments, obtaining the target biomechanical load distribution comprises receiving physiological objective data from a user input device, and calculating the target biomechanical load distribution in accordance with the physiological objective data.

The physiological objective may correspond to a primary objective to the user that includes any of: performance improvement, injury risk reduction, and improving health and fitness. Improving health and fitness may include improving any of: muscle strength, muscle tone, hormone production, calorific burn, weight loss, joint mobility, endurance capability or cardiovascular health in the user.

The method may further comprise obtaining physiological and biomechanical load data for the user, and obtaining the target biomechanical load distribution may comprise using the physiological objective data and the physiological and biomechanical load data to define a target by a mechanical load distribution as a set of measures for parameter values.

The method may also, in some embodiments, involve the alleviation or reduction of injury risk. In such embodiments, the method may further comprise calculating an injury risk parameter indicating an estimated probability of injury to the user occurring as a result of the action being performed, and may further comprise generating the motion adjustment instruction in accordance with the injury risk parameter. For example, such data may be obtained by the system indicating that a particular part of the body is susceptible to injury with a given degree of probability, and this probability may be related to or based upon a given biomechanical force applied to that body part. Thus the target biomechanical load distribution may be calculated so as to reduce the biomechanical load exerted upon a susceptible area in particular, or may adjust the distribution within the target biomechanical load distribution so as to minimise the overall probability of injury for one or more injury-susceptible body parts.

Therefore, the method may further comprise obtaining injury susceptibility data for the user, the injury susceptibility data including an indication of one more injury-susceptible parts of the body of the user in which biomechanical load is to be minimised. In such embodiments, obtaining the target biomechanical load distribution may comprise calculating the target biomechanical load distribution so as to minimise the forces that are exerted upon the one or more injury-susceptible parts as a result of the motion of the user. Typically, the indicated parts of the body correspond to joints or muscles that are susceptible to injury.

A user performing an action may wish to target particular parts of their body to be subjected to higher, or relatively high levels of physical exertion during performing the action. Some embodiments may accommodate this by way of the method further comprising obtaining target body part data for the user, the target body part data including an indication of one or more training parts of the body of the user in which biomechanical load is to be maximised. Obtaining the target biomechanical load distribution may comprise calculating the target biomechanical load distribution so as to maximise forces that are exerted upon the one or more training parts as a result of the motion of the user.

A user may specify particular training target body parts in order to improve performance of the activity. Thus, the indicated parts of the body may correspond to joints or muscles that are expected to improve performance in the activity, such that the target biomechanical load distribution is calculated so as to exercise or stress a specific anatomical structure to stimulate adaptations such as muscle growth, or to improve calorific burn through engaging specific muscle groups.

In some embodiments, the target biomechanical load is calculated so as to evenly distribute the forces that are exerted upon one or more parts of the body of the user as a result of the motion of the user, so as to reduce the onset of fatigue in a muscle group or joint and improve the endurance of the user in relation to the action.

In some situations, the user may perform an activity, such as walking or running in conditions that will affect their technique, such as their running technique. Examples of this may be running uphill, downhill, or across terrain that is uneven. Further examples of action performance-affecting conditions are softer surfaces such as grass or sand, harder surfaces such as concrete or asphalt, performing the action in a windy environment, or in extreme temperatures. In some embodiments therefore, for these cases, the base line profile, target profile, and incremental goal may be adjusted to reflect the influence of these external conditions on the runner or other type of user. Therefore, in some embodiments, the method further comprises obtaining environment data including an indication of the terrain and/or environmental conditions in which the user is performing the action. Calculating the target adjustment may then be performed in accordance with the target environment data.

In some embodiments, the method is suitable for helping a user alter their style of execution of the action, the method further comprising: recording sensor values from the sensor arrangement in a log file, determining instructions to change parameters that the user can directly influence, and outputting said instructions to said user, and further comprising calculating the current physical state of the user in terms of a profile of measures that includes a biomechanical load distribution for the body of the user, and using it to calculate an instruction that is output to the user, wherein the instruction requires the user to attempt to change at least one parameter in the next time interval and subsequent instructions after the next time interval depend on how the physical state has changed, in order to help the user achieve a particular physical state described by a target profile of measures.

In some embodiments, the method comprises performing a calculation after each interval to determine the goals for the next parameters that the user should attempt to change to produce the optimum benefit in progress towards the target profile.

In some embodiments, the method further comprises estimating the influence of performance during the performing of the action and using it to adjust the instruction.

Typically, the action is a sporting activity or a form of exercise. In many implementations, the action is related to running.

In some embodiments, the method comprises using machine learning to calculate the target adjustment and/or to generate the motion adjustment instruction.

In accordance with a third aspect of the invention there is provided a computer readable storage medium configured to store computer executable code that when executed by a computer configures the computer to: obtain a target biomechanical load distribution for the user, monitor, using data from a sensor arrangement, the motion of the user so as to obtain monitored motion data, calculate a monitored biomechanical load distribution for the user, in accordance with the monitored motion data, calculate a target adjustment to the motion of the user that corresponds to a reduction of a deviation of the monitored biomechanical load distribution from the target biomechanical load distribution, generate a motion adjustment instruction in accordance with the target adjustment.

BRIEF DESCRIPTION OF THE DRAWINGS

Examples of the present invention will now be described, with reference to the accompanying drawings, in which:

FIG. 4 is a diagram of a free body model for a single element which may be used in an example according to the invention;

FIG. 5 is a diagram of an anatomical model of an ankle/foot of a user which may be employed in an example according to the invention;

FIG. 7 is an example of a profile representing the physical state of a user that is measured by an example system according to the invention at regular intervals;

DESCRIPTION OF EMBODIMENTS

Figure 1:
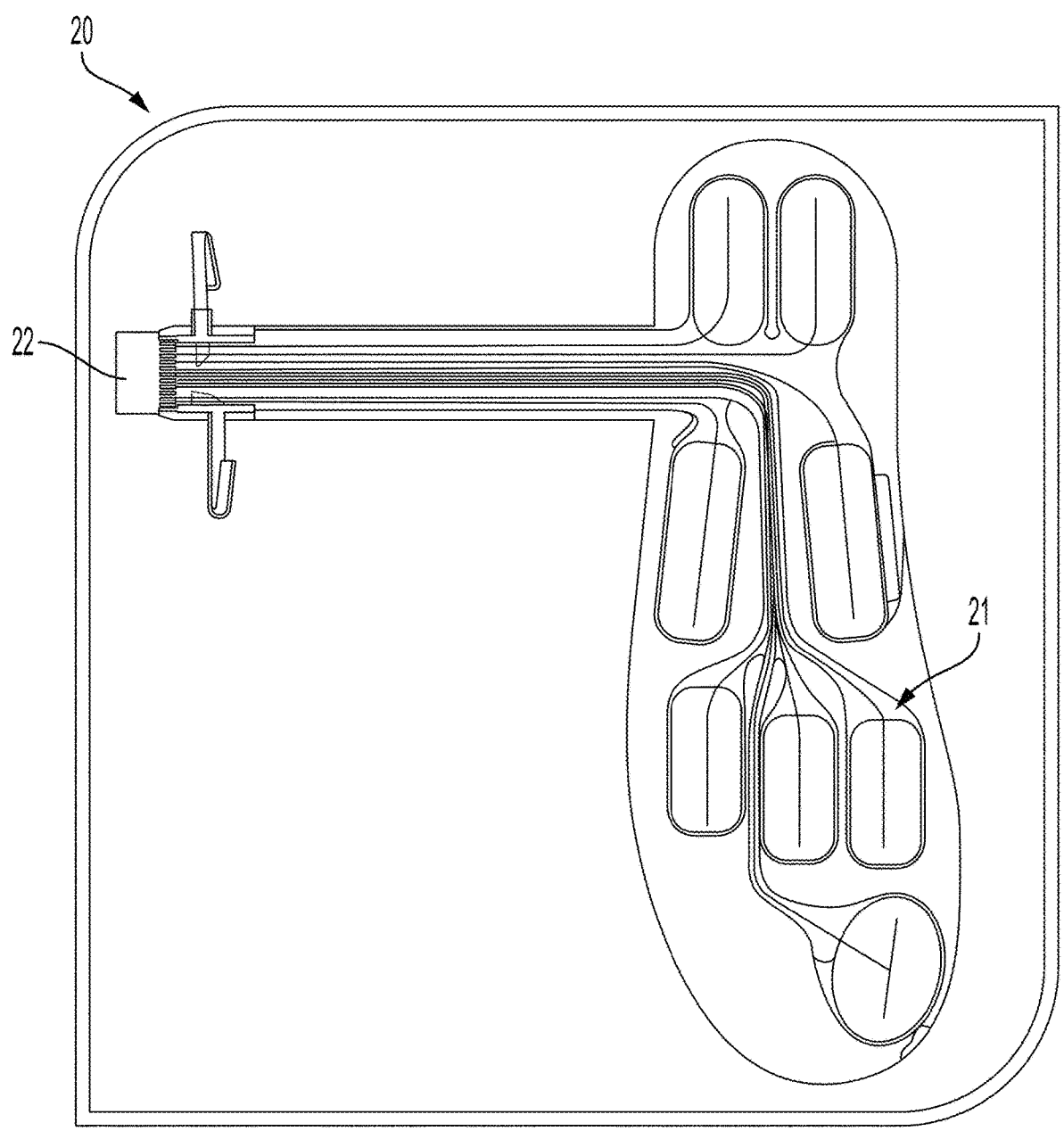
FIG. 1 shows a part of an example system according to the invention including a shoe insole with pressure sensors.
Figure 2:
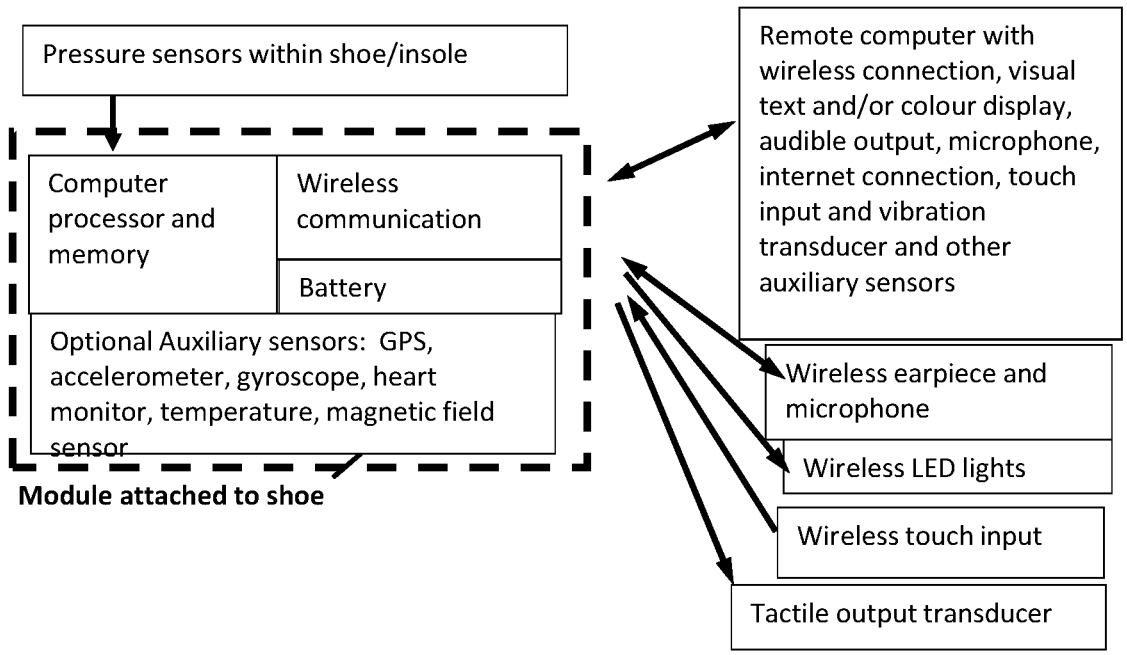
FIG. 2 is a box diagram depicting an example system according to the invention.
Figure 3:
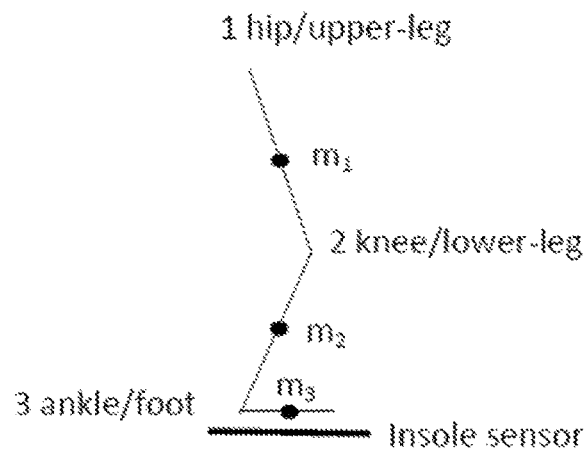
FIG. 3 is a diagram of a link segment model for the human leg which may be used in an example method according to the invention.

In a first example, the system uses data from the foot sensors in conjunction with a GPS location sensor, gyroscope and accelerometers. Further sensors such as a heart rate monitor can also be added to improve injury risk assessment and/or performance assessment. A schematic of the system is shown in FIG. 2.

A computer processor, memory and power supply are contained within a small module that is attached to the user's shoe. The module can communicate wirelessly with a remote computer that is used to input instructions to the coaching system. Typically, this remote computer can be a "smart phone", tablet or personal computer. Alternatively, input and output devices can communicate directly with the shoe module by wireless link. While the user is running, data can be stored in the shoe module or optionally transmitted to a remote computer and after the run the data can be read out to a remote computer for data analysis and presentation of coaching instructions to the user. Alternatively, the shoe module in combination with wirelessly-connected external devices can provide feedback and coaching instructions to the user at regular intervals while they are running. The system uses real time measurements and models to derive physiological and/or biomechanical parameters. In particular, the system can calculate an instantaneous numerical representation of the mechanical forces and torques/moments at different position in the body. This is the "biomechanical load distribution" and is calculated by using a mechanical model for the body and deriving the load, in terms of forces and moments on individual joints, from external sensor measurements. The system continues to measure and recalculate the forces and moments at regular intervals throughout a stride. One measure of the relative biomechanical load distribution at different locations is obtained by determining the average over the stride period for all the calculated values of force or moment for each location in the body. Alternative measures are possible such as the maximum, minimum, median, range or standard deviation over the stride period. The principles of inverse dynamics are well known (see for example en.wikipedia.org/wiki/Inverse_dynamics) where the body limbs are approximated by a link-segment model and forces and moments are computed from measurements of the motion of limbs and external forces such as ground reaction forces. The forces experienced by various segments or anatomical structures may also be calculated through statistical correlation parameters derived from measurements from a plethora of sensors mounted on the person, and population data from lab based measures and inverse dynamics. In this first embodiment measurements from spatially distributed pressure sensors, embedded in an insole, are used to calculate the forces experienced by the ankle joint and which muscle groups are most actively engaged to exert the moment/torque about the joint during the stance phase of running. Because there is no direct measurement of limb movement in this embodiment, the limb positions have to be deduced from the foot pressure measurements and the following example shows how this is achieved.

FIG. 4 shows the forces and moments operating on a single segment. In the bottom-up inverse dynamics procedure, the forces and moment for the distal joint, together with the mass, dimensions and acceleration of the segment are used to determine the forces and moment for the proximal joint, using the equations of motion. Equal and opposite reactive forces and moment for this proximal joint are then used as the forces and moment for the distal end of the next segment that is closer to the body. In the stance phase of running, the foot is contacting the ground and experiences a ground reaction force which is the first external force in the link segment chain. A more anatomical representation of the foot is needed to determine the forces and moments for the distal end of the foot and this is shown in FIG. 5.

During the stance phase in stable state running (no acceleration), a person is supporting the body on one foot with spatially distributed pressure sensors embedded in an insole under the supporting foot. The ground reaction force $R_{y,3}$ is measured via the spatially distributed pressure sensors embedded in the insole. The centre of pressure (COP) is calculated from the known positions of the pressure sensors in the insole and the model assumes all pressure to act through this calculated point. The total force acting through the COP can be derived from the foot pressure sensor measurements but the mass and position of COM of the foot segment have to be inferred from the person's available anthropometric data and population statistics. The angle of the foot is inferred from the pressure and position of the COP relative to the rest of the foot during the stance phase by using the correlation of angle (measured by a motion analysis system) with pressure and COP propagation for a representative population of runners. Similarly, the velocity and acceleration of the ankle can be estimated. This follows a similar statistical approach used for example by Mann et al (Gait & posture 39(1), August 2013, "Reliability and validity of pressure and temporal parameters recorded using a pressure-sensitive insole during running" www.researchgate.net/publication/256927941). For greater accuracy it is also possible to take measurements from an inertial measurement unit (IMU) mounted below the ankle joint (on the shoe if present) to determine angular rotation without needing to make statistical estimates.

In a specific example, at a particular point in time for a person, the COP is 0.03 m from the ankle joint. The force acting through the COP calculated from the pressure measurement ($R_{y3}$) is 686.7 N. The size of the foot is known from the size of the sensing insole and position of the sensors, thus, based on a scaling factor derived from average population statistics and the person's anthropometric data, the centre of mass is estimated to act 0.05 m from the ankle joint. The person's mass is 70 kg, and based on average population anthropometric data, the mass of the foot is 1 kg. In the position in time captured in FIG. 5, the foot is flat on the ground, $a_y=0$ and in steady state running, the acceleration $a_x=0$. Therefore, applying the equations of motion $R_{y3}$=686.7 N.

1. $\Sigma F_x = m \cdot a_x$, $R_{x3p} + R_{x3} = m \cdot a_x = 0$

2. $\Sigma F_y = m \cdot a_y$, $R_{y3p} + R_{y3} - m \cdot g = m \cdot a_y$ $R_{y3p} + 686.7 \text{ N} - 1 \times 9.8 = 0$ $R_{y3p} = -676.9$ N 3. About the COM, $\Sigma M_p = I_3 \cdot \alpha$, $M_p - R_{y3} \times (0.05 - 0.03) - R_{y3p} \times 0.05 = 0$ $M_p = 686.7 \times 0.02 + (-676.9 \times 0.05) = -33.85$ N·m In this example the net muscle moment $M_p$ is negative which indicates that the plantar flexor muscle groups are active in generating the moment/torque necessary to maintain the ankle angle. This means forces are experienced or exerted by the anatomical structures collectively commonly referred to as the "calf" which includes muscle groups such as the gastrocnemius, soleus, and tendons such as the Achilles and planta fascia.

The force and moment calculated for the proximal (ankle) end of the foot segment 3 is then used to calculate the equal and opposite reactive components used as input to the next segment in the biomechanical chain, namely segment 2 knee/lower-leg. The mass, length and COM of the leg are estimated from the person's available anthropometric data and population statistics. The angle of the knee can be estimated from the sensor measurements and any available anthropometric data for the person using correlations to kinematic data obtained by a motion capture system using a large population of runners. Thus, with the instantaneous estimates of heel position, velocity and acceleration, leg length and knee angle, the equations of motion can be solved to obtain the force and moment at the knee joint. In this case, the resulting muscle moment indicates how actively the quadriceps muscle groups are engaged. Optionally, additional measurements from an inertial measurement unit (IMU) mounted below the ankle joint (on the shoe if present) can be used to determine foot position and thus improve the correlation estimate of knee angle.

This process of using data from foot mounted sensors, anthropometric data and correlations established from kinematic studies on a large population of runners is used to estimate forces and moments for all the linked segments. The accuracy of these estimates decreases the further the limb segment is further from the foot but accuracy can be improved by adding further IMU sensors as in the next embodiment.

Figure 6:
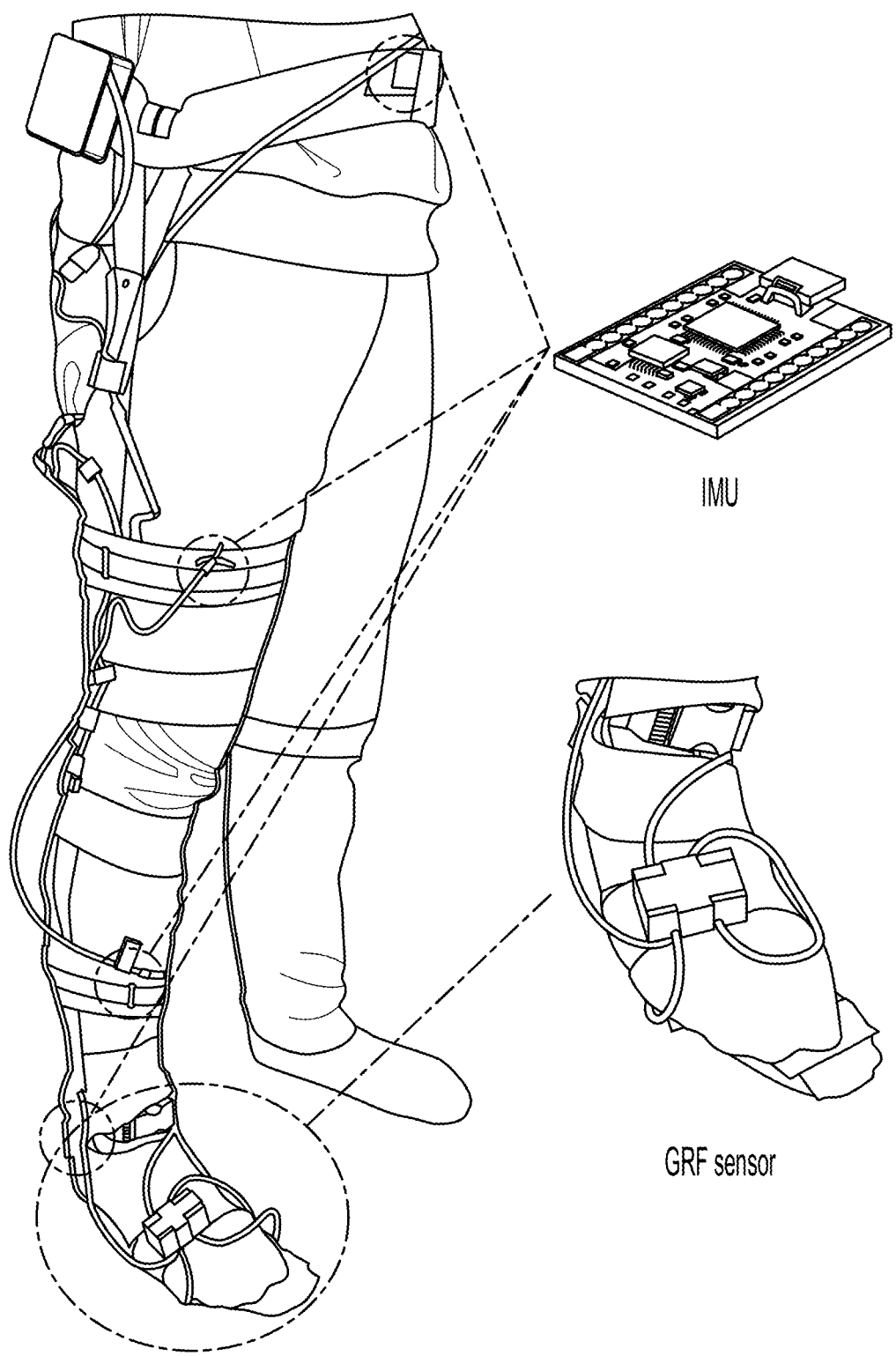
FIG. 6 contains photographs illustrating a system according to the invention containing IMUs attached to the body of a user and a ground reaction force (GRF) sensor attached to a foot of the user.

In a second embodiment, in addition to foot pressure sensors to measure ground contact forces, IMU sensors are connected to other parts of the body in order to get a more direct estimate of limb positioning, rather than having to use statistical correlation using measurements from a population of runners. In Kim et al "Estimation of Individual Muscular Forces of the Lower Limb during Walking Using a Wearable Sensor System" Hindawi Journal of Sensors Volume 2017, Article ID 6747921, IMUs are attached to the body as shown in FIG. 6 and are used to estimate limb positions and accelerations to enable muscular forces to be estimated.

In a third embodiment, only IMU sensors are used to determine body kinematics and no foot pressure sensor is employed. The number and placement of IMU sensors determines how accurately the biomechanical load distribution can be determined and statistical correlation modelling with a population of runners is required to estimate the ground reaction forces. This approach has also been applied to ski jumping for example (Logar and Munih, 2015, Sensors 2015, 15, 11258-11276; doi.org/10.3390/s150511258).

For any of the above embodiments, the system can calculate a "profile" that represents the physical state of the runner at a particular moment in time. A typical profile is shown in FIG. 7. Further physiological parameters can be obtained if suitable additional sensors are worn. For example, blood oxygen level can be estimated with an SpO2 monitor using light transmission through capillaries in the skin and breathing rate can be measured using an IMU strapped to the chest, or strain gauge embedded in the chest strap. The biomechanical parameters that the user can control can be used in coaching instructions but most of the parameters can only be measured by the system and cannot be directly controlled by the user.

The biomechanical load distribution indicates how much load is experienced by the joints and how much by the muscles and tendons. Joint load is generally related to segment forces and muscle/tendon loads are generally related to segment moments. The distribution can therefore indicate how hard muscles are working and which structures are exposed to extra loading and the related effects such as potential risk of injury.

Whereas the user will usually be able to alter aspects of their running style to change cadence, stride length, which part of foot makes initial contact with the ground, knee flexion, pre-tension of specific muscles such as abdominal muscles, leaning forward or backward, degree of pelvic rotation, reduce bounce in the run or adjusting the relative time they spend on each foot or how hard they push on each foot, they will find it more difficult or impossible to change physiological and/or biomechanical parameters such as, pronation, impulse, contact time, flight time or stability. Furthermore, if they successfully make a change, they will not know if they have succeeded in changing the biomechanical load distribution. Therefore, to provide effective coaching, the system provides instruction involving elements of running style that the user can directly control. This may also extend to choice of running shoes and other types of clothing that can influence running style.

Irrespective of the arrangement of sensors and method used to determine the biomechanical load distribution, the system gives the user the option of entering their own anthropometric data such as height, limb dimensions, weight and gender rather than the system relying on population averages. This data is used to scale the metrics to make them more relevant to the user. For example, stride length will be scaled to be a factor of the height or leg length of the user.

The system further gives the user the option of entering data on any previous injuries and when they occurred.

The system is either set up for a specific primary objective, or the system allows the user to choose a primary objective for their running activity. For example, performance objectives can be to improve speed or achieve longer distance capability. For injury risk reduction, the primary objective can be to reduce risk to injury of a specific part of the body such as foot and ankle or hip and back and the type of injury to be avoided such as soft or hard tissue. Health and fitness objectives can be losing weight, improving muscle tone, joint mobility, cardiovascular health or endurance capability for other activities for example.

Thus, the system obtains similar information from a user that a human coach would be requesting prior to commencing the coaching activity.

The system instructs the user to go for a run using their usual running style. During the run, the system monitors and records sensor outputs and derives measures of physiological and/or biomechanical parameters. In particular, the system calculates a biomechanical load distribution across the body inferred from the sensor measurements using a kinematic biomechanical model. Thus, after the run, the system has obtained a set of metrics that constitute a "baseline profile" for the user that includes the biomechanical load distribution. These metrics may also include strike Index (which part of foot makes initial contact with the ground), cadence (steps per minute), stride length, balance (which foot is used most), stability (how stable the foot is when in contact with the ground), impact (rate and magnitude of forces experienced by foot when hitting the ground), contact time (how long the foot remains in contact with the ground during each step), pronation (inward movement of foot as it rolls to distribute the force of striking the ground), vertical oscillation (measure of vertical motion while running), flight time (time when feet are in the air between steps). These metrics can be expressed as averages, maximum and minimum or variance over the recording period.

The system then calculates a "target profile" which involves the same metrics as the baseline profile and has values that will take the user closer to the primary objective and are expected to be attainable by the user based on prior research. If the primary objective is to improve performance, this may increase risk of injury and the results of prior research and any history of previous injury are used to calculate a target profile where the overall risk of injury to achieve the performance objective is minimised. If the primary objective is to reduce risk of injury, the target profile will be calculated to maintain a similar performance profile but reduce the risk of injury by taking into account any history of previous injury and prior research on injury risk. If the primary objective is for the user to lose weight or improve muscle tone, then the Target Profile will reflect a change in physiological and/or biomechanical activity that exercises muscle groups expected to produce a higher rate of calorie burn, hormone production or muscle groups that the user wants to strengthen or tone while minimising the risk of injury based on any history of previous injury and prior research on injury risk. The ability to calculate the biomechanical load distribution is critical to being able to assess specific anatomical structures, such as muscle groups, and find where the body is under stress. The system calculations make use of published research that relates physiological and/or biomechanical metrics to performance, risk of injury and health factors (See for example, "Foot strike patterns and collision forces in habitually barefoot versus shod runners"; Lieberman, Venkadesan, Werbel, Daoud, D'Andrea, Davis, Ojiambo Mang'Eni & Pitsiladis; Nature 463, 531-535 2010, "The effect of shoe type and fatigue on strike index and spatiotemporal parameters of running"; Mann, Malisoux, Urhausen, Statham, Meijer, Theisen; Gait Posture. 2015 June; 42(1):91-5 2015, "Biomechanics, Load Analysis and Sports Injuries in the Lower Extremities"; Nigg; Sports Medicine, Volume 2, Issue 5, pp 367-379 1985).

The calculations also take into account the change in physiological and/or biomechanical loading associated with a change in metrics. To reduce injury risk, the target profile is chosen to minimise loading or avoid loading sections of the biomechanical chain that aggravate particular injuries to which the user could be vulnerable.

Having determined a target profile, the system calculates an order of changes that the user is expected to be able to control in order to change their profile from baseline to target profile. To establish the order of changes, the system adopts one of a number of possible coaching strategies where parameters are categorised according to a selected skill classification and ordered according to a coaching or skill acquisition methodology. Examples of such coaching strategies and the principles of a hierarchical approach to coaching are in the following web references:

www.teachpe.com/sports_psychology/teaching.php
neurcscience.uth.tmc.edu/s3/chapter01.html
www.humanneurophysiology.com/motorunit.htm
www.aworkoutroutine.com/exercise-order/,
www.ptonthenet.com/articles/the-functional-continuum-3251
www.ideafit.com/fitness-library/functional-exerc-ise-progression
www.strengthandcondtioningresearch.com/perspectives/strength-endurance-continuum/

These coaching strategies usually use a hierarchical rule-based approach based on experience and specific studies. However, an alternative approach is to use machine learning principles to find the most effective way to instruct the user to achieve a desired physical state. By compiling data on the instructions and effects from a large population of runners using the system over time, new strategies can be developed rather than rely on published strategies and the method of calculating the target profile can be refined to avoid situations where it would be unattainable.

Figure 8:
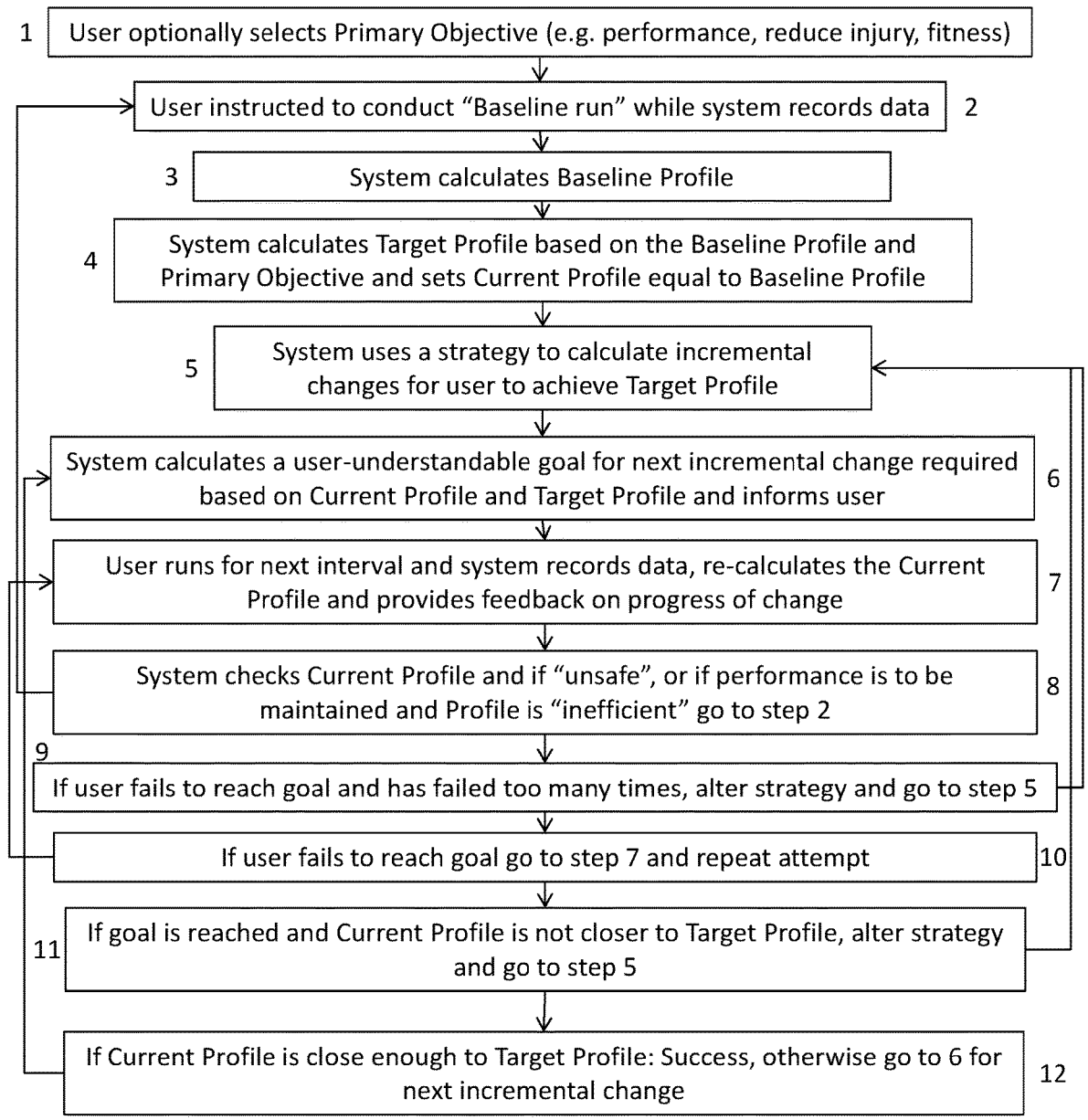
FIG. 8 is a flowchart illustrating an example coaching process provided by an example of the invention.

Having calculated an order, the system then instructs the user to conduct a run and attempt to change the first aspect of their running style to influence one or more parameters towards a goal value that may be automatically adjusted to account for terrain, ambient and environmental conditions. While the user is focussing on particular parameters, the system provides feedback on these parameters by audible, visible or vibration feedback and provides warnings if the user is making too large an incremental change that could increase injury risk or reduce performance. If that attempt is successful, the system instructs the user to change the next aspect in the order of changes and moves down the order until the user's current profile is near enough to the target profile (using a distance metric such as a sum of weighted squared differences in parameter values). If the user fails to achieve an incremental goal, the system invites them to repeat the attempt in another running interval. If the user fails to reach a particular incremental goal after a prescribed number of attempts, the coaching strategy is not working and the system goes back and uses the acquired data to modify the coaching strategy which may involve using an alternative classification for parameters or a different coaching or skill acquisition methodology. The system then prepares a new order of changes before instructing the user to make the next incremental change. While the user is focussing on making changes to one or more parameters, all other physiological and/or biomechanical parameters are checked to see if any changes have occurred that are likely to increase risk of injury beyond a predetermined threshold ("unsafe") or alternatively if the changes are likely to reduce performance ("inefficient"). If that is the case and current profile is considered to be either "unsafe" or "inefficient" the coaching session is terminated and the user is instructed to stop trying to make changes and, for the next running interval, to run using a running style the user finds comfortable. The system collects data during this run to form a new "baseline profile" and will calculate a new "target profile" and order of changes taking into account the data that has been acquired during all coaching sessions. The overall process is described by Steps 1-12 of the flow chart in FIG. 8. The "profile" is the collection of physiological and/or biomechanical parameter values including the biomechanical load distribution that quantify the person's physical state. A user-understandable goal involves a parameter that the user can influence directly.

Terrain and environmental conditions will affect how the runner will perform and this can be taken into account when baseline parameters are recorded and when incremental goals are set as suggested by the following examples. When the system measures high ambient temperatures or retrieves the temperature from another source such as the internet, it will reduce it will reduce speed/intensity goal values to account for additional thermal stress on the body (see for example, "Reductions in Cardiac Output, Central Blood Volume, and Stroke Volume with Thermal Stress in Normal Men during Exercise; Rowell, Marx, Bruce, Conn and Kusu"; Journal of Clinical Investigation Vol. 45, No. 11, 1966 or "Effect of Thermal Stress on Cardiac Function; Wilson and Crandall"; Exerc Sport Sci Rev. 39(1): 12-17 2011). If the system obtains data regarding the wind direction and the running direction of the user the system will adjust a speed goal to account, for example, for the additional effort required to run into the wind. Via GPS data, the system can detect if the user is running uphill and reduce the goal value of the stride length to account for the extra effort required to climb the incline. A balance goal value can be adjusted to account for a user running across an incline to account for the extra load the downhill foot has to endure compared to the uphill foot.

In a specific example, the operation of the system is now described for a runner who has declared a history of knee injuries to the system and wants to reduce injury risk. The prior research suggests that in general, high cadence, short stride length and mid or fore-foot strike index will reduce knee injury risk. Thus, if the baseline profile is not optimal the target profile will include changes to these parameters. "Cadence" is typical of a simple skill parameter that is under user control and likely to be high in the coaching order so using the coaching strategy gleaned from prior research, the system calculates a programme of incremental changes to cadence, stride length and strike index. Research (for example "Excessive progression in weekly running distance and risk of running-related injuries: an association which varies according to type of injury"; Nielsen, Parner, Nohr, Sørensen, Lind, Rasmussen; J Orthop Sports Phys Ther. 44(10):739-47 2014 or "Muscle activity and tibial shock during the initial transition from shod to barefoot running"; Gutierrez and Olin; International Society of Biomechanics Congress 2011 or "Barefoot-simulating footwear associated with metatarsal stress injury in 2 runners"; Giuliani, Masini, Alitz, Owens; Orthopedics. 7; 34(7):e320-3 2011) has shown that attempting to make large changes in running style is a major source of increased risk of injury so the coaching system advises small incremental changes. Therefore, such a user with a history of knee injuries would typically first be given an instruction by the system to "increase cadence by 5%" in the next running interval (They might alternatively be asked to "increase cadence and reduce stride length by 5% while maintaining the same running speed" but combination goals are only given if they help the user progress towards what they should be trying to achieve). If the user achieves this goal, the system compares the current profile to the target profile and if closer, moves to the next change down the order. If the user is currently striking close to the heel, the system will give the user an instruction such as "Attempt to move your foot contact point more towards the mid foot and toe" for the next running interval. If the user achieves all goals, the system compares the current profile to the target profile and if close enough the user will have successfully achieved a biomechanical loading profile with reduced loading on the knee and associated anatomical structures. Thus, without the intervention of a human coach, the system guides the user through a series of controlled incremental changes to help them alter their running style in a way which will take them closer to the primary objective of the coaching activity. Thus, the system provides unsupervised automated coaching that follows established coaching principles and in addition provides live monitoring and feedback of factors likely to influence risk of injury or performance. The sensors, computation machine and algorithms constitute an artificial intelligence advice module that can monitor the physical state and estimate the current biomechanical load distribution for the body and use that to calculate an instruction that the user will be able to execute.

The invention claimed is:

1. A computer-implemented method of generating a motion adjustment instruction for a user performing an activity, the method comprising:
   obtaining, via a computer, a target biomechanical load distribution for the user based on user data and a biomechanical load model,
   monitoring, using a sensor arrangement comprised of sensors positioned on one or more parts of a body of the user, motion of a portion of a body of the user so as to obtain monitored motion data,
   communicating the monitored motion data to the computer,
   calculating a monitored biomechanical load distribution for the user, in accordance with the monitored motion data and the biomechanical load model,
   calculating a target adjustment to the motion of the user that corresponds to a reduction of a deviation of the monitored biomechanical load distribution from the target biomechanical load distribution,
   generating a motion adjustment instruction in accordance with the target adjustment, and
   communicating the motion adjustment instruction to the user by displaying a visual message on a display, annunciating an audible message on an audible device, providing a haptic signal on a haptic device, or any combination of the foregoing,
   wherein the sensor arrangement comprises at least one of:
      one or more pressure sensors configured to monitor pressure exerted upon one or more regions of a foot of the user as a result of a contact force exerted upon that foot by ground during locomotion, and wherein the monitored motion data comprises data representative of the monitored pressure, one or more inertial measurement units, wherein each of the inertial measurement units is attachable to a part of the body or clothing of the user and is configured to monitor linear acceleration and a rotational rate of the part to which it is attached, and wherein the monitored motion data comprises data representative of the monitored linear acceleration and rotational rate from each of the plurality of inertial measurement units, or one or more sensors configured to monitor a velocity, an orientation, or both the velocity and the orientation of the one or more monitored parts of the body of the user during the performing of the action.

2. The computer-implemented method according to claim 1, wherein a biomechanical load distribution comprises data representative of a distribution of biomechanical loads within a portion of the body of the user of forces exerted upon the body as a result of the motion of the user.

3. The computer-implemented method according to claim 1, wherein the activity is locomotion and an indication of the target adjustment comprises an instruction to alter a gait of the locomotion.

4. The computer-implemented method according to claim 1, wherein the one or more monitored parts of the body include one foot or both feet of the user, and wherein the monitored motion data for the one foot or each of the feet comprises an indication of a velocity, an orientation, or both a velocity and an orientation of the one foot or each of the feet during a stance phase of a gait cycle.

5. The computer-implemented method according to claim 1, wherein obtaining the target biomechanical load distribution comprises receiving physiological objective data from a user input device, and calculating the target biomechanical load distribution in accordance with the physiological objective data, wherein the physiological objective data corresponds to a primary objective for the user that includes any of: performance improvement, injury risk reduction, and improving health and fitness.

6. The computer-implemented method according to claim 1, wherein the method further comprises obtaining physiological and biomechanical load data for the user, and wherein obtaining the target biomechanical load distribution comprises using physiological objective data and the physiological and biomechanical load data to define the target biomechanical load distribution as a set of measures for parameter values.

7. The computer-implemented method according to claim 1, wherein the method further comprises obtaining injury susceptibility data for the user, the injury susceptibility data including an indication of one or more injury-susceptible parts of the body of the user in which biomechanical load is to be minimized, and wherein obtaining the target biomechanical load distribution comprises calculating the target biomechanical load distribution so as to minimise forces that are exerted upon the one or more injury-susceptible parts as a result of the motion of the user.

8. The computer-implemented method according to claim 1, wherein the method further comprises obtaining target body part data for the user, the target body part data including an indication of one or more training target parts of the body of the user in which biomechanical load is to be maximized, and wherein obtaining the target biomechanical load distribution comprises calculating the target biomechanical load distribution so as to maximize forces that are exerted upon the one or more training target parts as a result of the motion of the user, wherein the indicated parts of the body correspond to joints or muscles that are expected to improve performance in the activity, such that the target biomechanical load distribution is calculated so as to exercise or stress a specific anatomical structure to stimulate adaptations such as muscle growth, to improve calorific burn through engaging specific muscle groups, or to reduce onset of fatigue in a muscle group or joint and improve endurance of the user in relation to the action.

9. The computer-implemented method according to claim 1, wherein the action is a sporting activity or form of exercise and is related to running.

10. The computer-implemented method according to claim 1, comprising using results of machine learning from data on instructions and effects from a large population of runners to calculate the target adjustment, to generate the motion adjustment instruction, or to calculate the target adjustment and to generate the motion adjustment instruction.

11. The computer-implemented method of claim 1, wherein the sensor arrangement comprises the one or more pressure sensors configured to monitor pressure exerted upon one or more regions of a foot of the user as a result of a contact force exerted upon that foot by ground during locomotion.

12. The computer-implemented method of claim 1, wherein the sensor arrangement comprises the one or more inertial measurement units.

13. The computer-implemented method of claim 1, wherein the sensor arrangement comprises the one or more sensors configured to monitor a velocity, an orientation, or both a velocity and an orientation of the one or more monitored parts of the body of the user during the performing of the action.

14. A non-transitory computer readable storage medium storing computer executable code that when executed by a computer configures the computer to:

obtain a target biomechanical load distribution for a user using user data and a body-segment biomechanical load model;

monitor, using data from a sensor arrangement comprised of sensors positioned on one or more parts of a body of the user, motion of the user so as to obtain monitored motion data;

calculate a monitored biomechanical load distribution for the user, in accordance with the monitored motion data;

calculate a target adjustment to the motion of the user that corresponds to a reduction of a deviation of the monitored biomechanical load distribution from the target biomechanical load distribution;

generate a motion adjustment instruction in accordance with the target adjustment, the target adjustment to the motion of the user that corresponding to a reduction of a deviation of the monitored biomechanical load distribution from the target biomechanical load distribution, the reduction being less than the deviation; and display a visual message on a display, annunciate an audible message on an audible device, provide a haptic signal on a haptic device, or any combination of the foregoing, wherein the sensor arrangement comprises at least one of:
at least one pressure sensor that is configured to monitor pressure exerted upon one or more regions of a foot of the user as a result of a contact force exerted upon that foot by ground during locomotion, and wherein the monitored motion data comprises data representative of the monitored pressure, one or more inertial measurement units, wherein each of the inertial measurement units is attachable to a part of the body or clothing of the user and is configured to monitor linear acceleration and a rotational rate of the part to which it is attached, and wherein the monitored motion data comprises data representative of the monitored linear acceleration and rotational rate from each of the inertial measurement units, or one or more sensors configured to monitor a velocity, an orientation, or both a velocity and an orientation of the one or more monitored parts of the body of the user during the performing of the action.

15. The non-transitory computer readable storage medium of claim 14, wherein the sensor arrangement comprises the one or more sensors configured to monitor a velocity and orientation of the one or more monitored parts of the body of the user during the performing of the action.

16. The non-transitory computer readable storage medium of claim 14, wherein the sensor arrangement comprises the plurality of inertial measurement unit sensors of an inertial measurement unit, the one or more inertial measurement unit sensors being configured to monitor a linear, angular, or both linear and angular velocity, acceleration, or velocity and acceleration in a plurality of spatial axes.

17. The non-transitory computer readable storage medium of claim 14, wherein the sensor arrangement comprises the one or more pressure sensors.

18. The non-transitory computer readable storage medium according to claim 14, wherein the body-segment biomechanical load model is a link-segment model.

19. The non-transitory computer readable storage medium according to claim 14, wherein the body-segment biomechanical load model is a statistical correlation model.

20. A system comprising:
one or more computer processors;
a computer executable instruction storage medium in communication with the one or more computer processors;
a sensor arrangement in communication with the one or more computer processors, the sensor arrangement comprised of sensors positioned on one or more parts of a body of a user so as to generate motion data of the user;
an input device via which the user can input user data; and
computer executable instructions stored in the storage medium that when executed by the one or more computer processors cause the system to:
obtain the user data from the input device,
monitor, via the sensor arrangement, motion of the one or more body parts of the user so as to obtain the monitored motion data of the user,
calculate a monitored biomechanical load distribution for the user, in accordance with the monitored motion data and a biomechanical load model,
obtain a target biomechanical load distribution for the user based on the user data and the biomechanical load model,
calculate a target adjustment to the motion of the user that corresponds to a reduction of a deviation of the monitored biomechanical load distribution from the target biomechanical load distribution, the reduction being less than the deviation,
generate a motion adjustment instruction in accordance with the target adjustment, and
display the motion adjustment instruction on a display which is viewable by the user, annunciate the motion adjustment instruction on an audible device, provide a haptic signal on a haptic device, or any combination of the foregoing,
wherein the sensor arrangement comprises at least one of:
one or more pressure sensors configured to monitor pressure exerted upon one or more regions of a foot of the user as a result of a contact force exerted upon that foot by ground during locomotion, and wherein the monitored motion data comprises data representative of the monitored pressure,
one or more inertial measurement units, wherein each of the inertial measurement units is attachable to a part of the body or clothing of the user and is configured to monitor linear acceleration and a rotational rate of the part to which it is attached, and wherein the monitored motion data comprises data representative of the monitored linear acceleration and rotational rate from each of the inertial measurement units, or
one or more sensors configured to monitor a velocity, an orientation, or both a velocity and an orientation of the one or more monitored parts of the body of the user during the performing of the action.

21. The system according claim 20, wherein, when executed by the one or more computer processors, the computer executable instructions stored in the storage medium cause the system to calculate the monitored biomechanical load distribution by calculating values for a magnitude and direction of forces exerted upon a plurality of parts of the body of the user, based upon the monitored motion data and using a computational mechanical model of the body of the user.

22. The system according to claim 20, wherein the sensor arrangement comprises the one or more pressure sensors configured to monitor pressure exerted upon one or more regions of a foot of the user as a result of a contact force exerted upon that foot by ground during locomotion.

23. The system according to claim 20, wherein the sensor arrangement comprises the one or more sensors configured to monitor the velocity the orientation, or both the velocity and the orientation of the one or more monitored parts of the body of the user during the performing of the action.

24. The system according to claim 20, wherein, when executed by the one or more processors, the computer executable instructions cause the system to identify one or more parameters defining the motion of the user and generate the motion adjustment instruction by computing, based upon the target adjustment, a change to a value of at least one of the one or more parameters such that the change can be executed by the user in performing the action so as to result in the target adjustment.

25. The system according to claim 20, wherein the sensor arrangement comprises the one or more inertial measurement units, wherein each inertial measurement unit is attachable to a part of the body or clothing of the user and is configured to monitor linear acceleration and a rotational rate of the part to which it is attached.

* * * * *